US008288583B2

(12) United States Patent
Boehmke et al.

(10) Patent No.: US 8,288,583 B2
(45) Date of Patent: Oct. 16, 2012

(54) PROCESS FOR PREPARING CARBOXYLIC ACID DERIVATIVES

(75) Inventors: Uwe Boehmke, Darmstadt (DE); Klaus Schimossek, Bensheim (DE); Detlef Bloos, Eberbach (DE); Michael Neusius, Darmstadt (DE); Stephan Massoth, Biblis (DE); Guenther Graeff, Alsbach-Haehnlein (DE); Alexander Dardin, Laudenbach (DE); Matthias Fischer, Floersheim-Dalsheim (DE); Volker Stephan, Brensbach (DE)

(73) Assignee: Evonik Rohmax Additives GmbH, Darmstadt (DE)

( * ) Notice: Subject to any disclaimer, the term of this patent is extended or adjusted under 35 U.S.C. 154(b) by 385 days.

(21) Appl. No.: 12/306,019

(22) PCT Filed: Jun. 1, 2007

(86) PCT No.: PCT/EP2007/055373
§ 371 (c)(1),
(2), (4) Date: Dec. 22, 2008

(87) PCT Pub. No.: WO2008/022823
PCT Pub. Date: Feb. 28, 2008

(65) Prior Publication Data
US 2009/0182145 A1 Jul. 16, 2009

(30) Foreign Application Priority Data

Aug. 23, 2006 (DE) .......................... 10 2006 039 420

(51) Int. Cl.
*C07C 67/02* (2006.01)
(52) U.S. Cl. .................................................... 560/217
(58) Field of Classification Search .................. None
See application file for complete search history.

(56) References Cited

U.S. PATENT DOCUMENTS

| | | | | |
|---|---|---|---|---|
| 3,887,609 | A * | 6/1975 | Strehlke et al. | 560/217 |
| 4,658,002 | A * | 4/1987 | Tschang et al. | 526/264 |
| 4,777,265 | A | 10/1988 | Merger et al. | |
| 5,254,632 | A | 10/1993 | Kerscher et al. | |
| 5,760,265 | A | 6/1998 | Takahara et al. | |
| 6,080,794 | A | 6/2000 | Auschra et al. | |
| 6,409,778 | B1 | 6/2002 | Auschra et al. | |
| 6,458,750 | B1 | 10/2002 | Dardin et al. | |
| 6,639,099 | B1 | 10/2003 | Knebel et al. | |
| 6,736,981 | B2 * | 5/2004 | Gomez et al. | 210/777 |
| 7,429,555 | B2 | 9/2008 | Scherer et al. | |
| 7,452,932 | B2 | 11/2008 | Scherer et al. | |
| 2002/0121488 | A1 * | 9/2002 | Witteler et al. | 210/777 |
| 2005/0148749 | A1 | 7/2005 | Scherer et al. | |
| 2006/0142168 | A1 | 6/2006 | Kinker et al. | |
| 2006/0189490 | A1 | 8/2006 | Dardin et al. | |
| 2007/0191238 | A1 | 8/2007 | Fischer et al. | |
| 2007/0213237 | A1 | 9/2007 | Scherer et al. | |
| 2007/0219101 | A1 | 9/2007 | Scherer et al. | |
| 2008/0132663 | A1 | 6/2008 | Acker et al. | |
| 2008/0146475 | A1 | 6/2008 | Mueller et al. | |
| 2008/0194443 | A1 | 8/2008 | Stohr et al. | |
| 2008/0194861 | A1 | 8/2008 | Schmitt et al. | |
| 2008/0300373 | A1 | 12/2008 | Schmitt et al. | |
| 2009/0064568 | A1 | 3/2009 | Stohr et al. | |

FOREIGN PATENT DOCUMENTS

| | | |
|---|---|---|
| DE | 196 02 941 | 2/1997 |
| EP | 0 236 994 | 9/1987 |
| EP | 0 522 376 | 1/1993 |
| EP | 0 574 260 | 12/1993 |
| GB | 1 012 817 | 12/1965 |
| WO | 2004 108795 | 12/2004 |

OTHER PUBLICATIONS

U.S. Appl. No. 11/995,949, filed Jan. 17, 2008, Stoehr, et al.
U.S. Appl. No. 12/668,209, filed Jan. 8, 2010, Stoehr, et al.
U.S. Appl. No. 61/186,744, filed Jun. 12, 2009, Radano, et al.
U.S. Appl. No. 12/672,231, filed Feb. 4, 2010, Stoehr, et al.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to processes for preparing carboxylic acid derivatives, comprising the reaction of at least one carboxylic acid and/or of a carboxylic acid derivative with at least one alcohol and/or an amine in the presence of a metal-containing catalyst, wherein, after the reaction has ended, the metal-containing catalyst is contacted with water and a superabsorbent, the contacting of the catalyst with the water leading to hydrolysis of the catalyst. The present invention further relates to the use of superabsorbents for removing a metal-containing catalyst from a mixture after hydrolysis of the catalyst.

19 Claims, No Drawings

PROCESS FOR PREPARING CARBOXYLIC ACID DERIVATIVES

The present invention relates to processes for preparing carboxylic acid derivatives. The present invention further relates to the use of superabsorbents.

Carboxylic acid derivatives, especially esters and amides of carboxylic acids, are frequently obtained by transesterification or ester-amide exchange from one of the more easily obtainable esters of these carboxylic acids. In addition, these derivatives can in many cases also be prepared from carboxylic acid anhydrides by the reaction with an alcohol or an amine.

For catalytic acceleration of this reaction, various catalyst types have been proposed, for example, as well as acid and base catalysis, also catalysis by means of various metal compounds, especially lithium, aluminum, titanium, zirconium, tin and lead compounds. The latter processes are an option especially for preparing esters of more complex alcohols, for example the ester of heterocyclic alcohols [cf. H. Rauch-Puntigam, Th. Völker, Acryl-und Methacrylverbindungen [Acrylic and Methacrylic Compounds], p. 31-68, Springer-Verlag 1967, U.S. Pat. Nos. 2,138,763; 4,777,265; 5,210,177; EP-A 453638; U.S. Pat. No. 4,745,213; EP-A 571 851; DE-A 4301 673; J. Org. Chem. 22, 787-789 (1957)].

As well as the ever acute risk of formation of by-products (for example addition of alcohol onto any double bond present) and of unintended polymerization if the carboxylic acid comprises a double bond, problems occur in particular in the workup of the reaction mixture. For instance, the catalysts used in many cases have to be separated from the products, since the catalysts can have undesired effects in the products.

The above-described catalysts, especially titanium-and zirconium-comprising catalysts, can be precipitated by a hydrolysis and then removed from the reaction mixture by suitable methods. For example, publication DE-A-19602941 describes the preparation of esters and amides of (meth) acrylic acid. A disadvantage of this process is especially the high energy intensity which is required for centrifugation.

Furthermore, document U.S. Pat. No. 5,760,265 describes processes for preparing carboxylic esters, in which titanium- or zirconium-comprising catalysts are used. According to this publication, the catalysts are removed either by filtration using filtering aids, for example activated carbon, or by adding water which comprises chelating agents, for example EDTA. A disadvantage of the first method is the use of large amounts of filtering aids. Furthermore, it is found that a filtration with a fine-pore filter is very time-consuming. However, the use of smaller amounts of filtering aids or of coarse-pore filters does not lead to sufficient removal of the catalyst. The second method, in which the hydrolyzed catalyst is removed from the ester in the aqueous phase, is likewise afflicted with disadvantages. These include, more particularly, the addition of large amounts of water, in order to remove the complexed catalyst completely from the hydrophobic phase. The product specifications of most commercial esters accordingly require a costly and inconvenient drying step. In addition, most of the complexing agents described in U.S. Pat. No. 5,760,265 are expensive and questionable from an ecological point of view.

In addition, publication U.S. Pat. No. 4,505,091 describes processes for removing metal-comprising catalysts, in which amine or phosphorus compounds which serve as chelating agents are used. However, this process necessarily comprises a steam distillation, though not all reaction mixtures can be subjected to a steam distillation, since some products can react with water. This is true especially of esters which have a double bond onto which water can add, for example esters of acrylic acid or methacrylic acid. Furthermore, in this process, a large amount of energy is used for the steam distillation. Moreover, in this process too, a large amount of water is used for the purification, and so this process too can require a drying step.

Publication DE-A 42 17 124 sees one approach to avoiding the problem of the metal compounds which occur, especially of the metal hydroxides which occur in the case of hydrolytic decomposition, in the use of alkali metal and/or alkaline earth metal compounds. A particular advantage of the novel process, is claimed to be that, without addition of water or other separating agents, a successful separation of solid catalyst and liquid reaction products is possible, for example, by filtration. However, the use of this catalyst system may lead to formation of undesired by-products.

In the light of the prior art, it is thus an object of the present invention to provide processes for preparing carboxylic acid derivatives, especially carboxylic esters and carboxamides, which can be performed in a particularly simple and inexpensive manner, and with high yield. A particular problem consisted especially in providing a process for removing particularly appropriate catalysts, which ensures reliable and substantially complete removal of the catalysts with high speed, low energy input and is low yield losses.

These objects and further objects which are not stated explicitly, but which are immediately derivable or discernable from the connections discussed herein by way of introduction, are achieved by a process having all the features of claim 1. Appropriate modifications to the processes according to the invention are protected in subclaims.

By virtue of contacting, after a reaction of a carboxylic acid and/or a carboxylic acid derivative with an alcohol and/or an amine has ended, the metal-containing catalyst used with water and a superabsorbent, said contacting of the catalyst with the water leading to hydrolysis of the catalyst, a process for preparing carboxylic acid derivatives is provided, which can be performed in a particularly simple and inexpensive manner and with high yield.

At the same time, the processes according to the invention allow a series of further advantages to be achieved. One of these is that the process according to the invention makes it possible to remove particularly appropriate catalysts from the reaction mixture with high speed, low energy input and low yield losses, while ensuring reliable and essentially complete removal of the catalysts.

The process according to the invention enables the efficient preparation of carboxylic acid derivatives. In this process, especially carboxylic acids or derivatives thereof are used. Carboxylic acids comprise at least one group of the formula —COOH. Derivatives of carboxylic acids include especially carboxylic esters, carboxamides and carboxylic anhydrides. These compounds are known in the technical field and are described, for example, in Römpp Chemie Lexikon, 2nd edition on CD-ROM.

The reactants used may especially be aliphatic or cycloaliphatic carboxylic acids, saturated or unsaturated carboxylic acids, and aromatic carboxylic acids or derivatives thereof. The carboxylic acids or carboxylic acid derivatives for use as reactants may have one, two or more carboxylic acid groups or derivatives of these groups.

The particularly preferred carboxylic acids include especially methacrylic acid, acrylic acid, fumaric acid, maleic acid, oleic acid, stearic acid, oxalic acid, benzoic acid, phthalic acid, isophthalic acid, terephthalic acid and trimellitic acid.

The preferred derivatives which can be used as reactants include especially the anhydrides and esters of alcohols having from 1 to 6, and especially from 1 to 4 carbon atoms, for example the esters of methanol, ethanol, propanol, butanol, pentanol or hexanol of the acids listed above.

In a particular aspect of the present invention, it is possible with preference to use especially phthalic anhydride and/or maleic anhydride, and also methyl methacrylate, ethyl methacrylate, propyl methacrylate, butyl methacrylate, methyl acrylate, ethyl acrylate, propyl acrylate, butyl acrylate, monomethyl fumarate, dimethyl fumarate, monoethyl fumarate, diethyl fumarate, monomethyl maleate, dimethyl maleate, monoethyl maleate and/or diethyl maleate. It is possible with particular preference to use especially methacrylic acid, acrylic acid, and derivatives thereof, for example methyl methacrylate, ethyl methacrylate, propyl methacrylate, butyl methacrylate, methyl acrylate, ethyl acrylate, propyl acrylate and/or butyl acrylate.

As well as the above-described carboxylic acids or carboxylic acid derivatives, at least one alcohol and/or an amine is used as a reactant in the processes according to the invention. The alcohols and/or amines for use are not subject to any particular restriction, and so low molecular weight and/or high molecular weight compounds can be used. Both polar and nonpolar starting compounds are suitable here. These reactants are known in the technical field and are described inter alia, in the patent literature cited above as prior art.

One preferred compound class includes alcohols and/or amines which have from 1 to 50, preferably from 6 to 40 and more preferably from 8 to 30 carbon atoms. These include especially methylamine, dimethylamine, ethylamine, diethylamine, propylamine, dipropylamine, N-dimethylaminomethylamine, 2-diethylaminoethanol, 2-hydroxyethanol, 2-hydroxypropanol, 2,3-dihydroxypropanol, 2-(2-hydroxyethyl)imidazole, 4-(2-hydroxyethyl)morpholine, hexanol, heptanol, octanol, 2-ethylhexanol, nonanol, decanol, undecanol, dodecanol, tridecanol, tetradecanol, pentadecanol, hexadecanol, octadecanol, eicosanol, cetyleicosanol, stearyleicosanol.

A further group of alcohols and amines includes oligomeric or polymeric compounds which have at least one hydroxyl and/or amine functionality. These include especially polymers having a weight average of the molecular weight $M_w$ in the range from 500 to 100 000 g/mol. This parameter can be measured by gel permeation chromatography (GPC).

These polymers include especially functional polyolefins, which are described inter alia in EP-A-0 621 293 and EP-A-0 699 694. In addition, this group includes hydroxyl-terminated polyalkyl methacrylates, which are described in U.S. Pat. No. 5,254,632, DE-A 41 21 811 or EP-A 291 662.

In a particular aspect of the present invention, it is possible to use monohydric alcohols and/or monofunctional amines. The term "monohydric" means that the alcohol has exactly one hydroxyl group, and the term "monofunctional" that the amine has exactly one amino group. In a further aspect, it is possible in particular also to use alcohols and/or amines which have two or more hydroxyl and/or amino groups. In this case, these groups may have the same reactivity or a different reactivity in relation to the reaction with the carboxylic acid and/or the carboxylic acid derivative.

Further reactants arise from the products of the process according to the invention listed by way of example, which are listed below.

The preferred products of the process according to the invention include compounds which have at least one polymerizable double bond, for example (meth)acrylates, fumarates and maleates which derive from saturated alcohols, such as ethyl (meth)acrylate, n-propyl (meth)acrylate, isopropyl (meth)acrylate, n-butyl (meth)acrylate, tert-butyl (meth)acrylate and pentyl (meth)acrylate, hexyl (meth)acrylate, 2-ethylhexyl (meth)acrylate, heptyl (meth)acrylate, 2-tert-butylheptyl (meth)acrylate, octyl (meth)acrylate, 3-isopropylheptyl (meth)acrylate, nonyl (meth)acrylate, decyl (meth)acrylate, undecyl (meth)acrylate, 5-methylundecyl (meth)acrylate, dodecyl (meth)acrylate, 2-methyldodecyl (meth)acrylate, tridecyl (meth)acrylate, 5-methyltridecyl (meth)acrylate, tetradecyl (meth)acrylate, pentadecyl (meth)acrylate, hexadecyl (meth)acrylate, 2-methylhexadecyl (meth)acrylate, heptadecyl (meth)acrylate, 5-isopropylheptadecyl (meth)acrylate, 4-tert-butyloctadecyl (meth)acrylate, 5-ethyloctadecyl (meth)acrylate, 3-isopropyloctadecyl (meth)acrylate, octadecyl (meth)acrylate, nonadecyl (meth)acrylate, eicosyl (meth)acrylate, cetyleicosyl (meth)acrylate, stearyleicosyl (meth)acrylate, docosyl (meth)acrylate and/or eicosyltetratriacontyl (meth)acrylate;

cycloalkyl (meth)acrylates such as cyclopentyl (meth)acrylate, cyclohexyl (meth)acrylate, 3-vinylcyclohexyl (meth)acrylate, bornyl (meth)acrylate 2,4,5-tri-t-butyl-3-vinylcyclohexyl (meth)acrylate, 2,3,4,5-tetra-t-butylcyclohexyl (meth)acrylate;

(meth)acrylates which derive from unsaturated alcohols, such as 2-propynyl (meth)acrylate, allyl (meth)acrylate, vinyl (meth)acrylate, oleyl (meth)acrylate; and also the corresponding fumarates and maleates;

hydroxyalkyl (meth)acrylates, such as
3-hydroxypropyl (meth)acrylate,
3,4-dihydroxybutyl (meth)acrylate,
2-hydroxyethyl (meth)acrylate,
2-hydroxypropyl (meth)acrylate,
2,3-dihydroxypropyl (meth)acrylate,
2,5-dimethyl-1,6-hexanediol (meth)acrylate,
1,10-decanediol (meth)acrylate;
aminoalkyl (meth)acrylates, such as
2-diethylaminoethyl (meth)acrylate,
2-trimethylammonioethyl (meth)acrylate salt,
3-diethylaminopentyl (meth)acrylate,
3-dibutylaminohexadecyl (meth)acrylate;
aryl (meth)acrylates, such as benzyl (meth)acrylate or phenyl (meth)acrylate, where the aryl radicals may each be unsubstituted or up to tetrasubstituted;
carbonyl-containing (meth)acrylates, such as 2-carboxyethyl (meth)acrylate,
carboxymethyl (meth)acrylate,
oxazolidinylethyl (meth)acrylate,
N-(methacryloyloxy)formamide,
acetonyl (meth)acrylate,
N-methacryloylmorpholine,
N-methacryloyl-2-pyrrolidinone,
N-(2-methacryloyloxyethyl)-2-pyrrolidinone,
N-(3-methacryloyloxypropyl)-2-pyrrolidinone,
N-(2-methacryloyloxypentadecyl)-2-pyrrolidinone,
N-(3-methacryloyloxyheptadecyl)-2-pyrrolidinone;
glycol di(meth)acrylates, such as 1,4-butanediol (meth)acrylate, 2 butoxyethyl (meth)acrylate,
2-ethoxyethoxymethyl (meth)acrylate,
2-ethoxyethyl (meth)acrylate;
(meth)acrylates of ether alcohols, such as
tetrahydrofurfuryl (meth)acrylate,
vinyloxyethoxyethyl (meth)acrylate,
methoxyethoxyethyl (meth)acrylate,
1-butoxypropyl (meth)acrylate,
1-methyl-(2-vinyloxy)ethyl (meth)acrylate,
cyclohexyloxymethyl (meth)acrylate, methoxymethoxyethyl (meth)acrylate,
benzyloxymethyl (meth)acrylate,
furfuryl (meth)acrylate,
2-butoxyethyl (meth)acrylate,
2-alkoxymethylethyl (meth)acrylate, such as 2-methoxymethylethyl (meth)acrylate, 2-ethoxymethylethyl (meth)acrylate, 2-(iso)propoxymethylethyl (meth)acrylate, 2-butoxymethylethyl (meth)acrylate, 2-hexoxyethyl (meth)acrylate, 2-(2-hexoxyethoxy)ethyl (meth)acrylate, 2-ethoxyethoxymethyl (meth)acrylate,
2-ethoxyethyl (meth)acrylate,
allyloxymethyl (meth)acrylate,
1-ethoxybutyl (meth)acrylate,
methoxymethyl (meth)acrylate,
1-ethoxyethyl (meth)acrylate,
ethoxymethyl (meth)acrylate,
(meth)acrylic esters of polyoxyethylene oxide ether alcohols, for example the (meth)acrylic esters of methoxypolyethylene glycol, nonylphenoxypolyethylene glycol (MARLIPAL products from Hüls AG), amine-substituted ether-containing esters of (meth)acrylic acid, for example 2-(dimethylamino)ethoxyethyl (meth)acrylate;
(meth)acrylates of halogenated alcohols, such as
2,3-dibromopropyl (meth)acrylate,
4-bromophenyl (meth)acrylate,
1,3-dichloro-2-propyl (meth)acrylate,
2-bromoethyl (meth)acrylate,
2-iodoethyl (meth)acrylate,
chloromethyl (meth)acrylate;
(meth)acrylic esters of oxo alcohols;
oxiranyl (meth)acrylates, such as
2,3-epoxybutyl (meth)acrylate,
3,4-epoxybutyl (meth)acrylate,
10,11-epoxyundecyl (meth)acrylate,
10,11-epoxyhexadecyl (meth)acrylate,
2,3-epoxycyclohexyl (meth)acrylate;
glycidyl (meth)acrylate;
phosphorus-, boron-and/or silicon-containing (meth)acrylates, such as
2-(dimethylphosphato)propyl (meth)acrylate,
2-(ethylenephosphito)propyl (meth)acrylate,
dimethylphosphinomethyl (meth)acrylate,
dimethylphosphonoethyl (meth)acrylate, 2-(dibutylphosphono)ethyl (meth)acrylate,
2,3-butylene(meth)acryloylethyl borate,
methyldiethoxy(meth)acryloylethoxysilane,
diethylphosphatoethyl (meth)acrylate;
heterocyclic (meth)acrylates, such as
2-(1-imidazolyl)ethyl (meth)acrylate, 2-(4-morpholinyl)ethyl (meth)acrylate and 1-(2-(meth)acryloyloxyethyl)-2-pyrrolidone;
(meth)acrylamides, such as
N-(3-dimethylaminopropyl)(meth)acrylamide,
N-(2-hydroxyethyl)(meth)acrylamide,
N-(3-hydroxy-2,2-dimethylpropyl)(meth)acrylamide,
N-dimethylaminomethyl(meth)acrylamide;
quaternary ammonium compounds such as N-trimethylammoniumpropyl-(meth)acrylamide salt;
sulfonic acid derivatives such as 2-(meth)acrylamido-2-methylpropanesulfonic acid or N-(meth)acryloylurea.

The expression "(meth)acrylates" includes methacrylates and acrylates, and mixtures of the two.

The process according to the invention is of particular interest with regard to the preparation of polymers with free double bonds. Reference is made especially to the preparation process for macromonomers by transesterifying alkyl (meth)acrylate monomers with hydroxyl-terminated polyalkyl methacrylate, which are described in documents U.S. Pat. No. 5,254,632 or DE-A 41 21 811 and EP-A 291 662.

The process of U.S. Pat. No. 5,254,632, which can be combined particularly successfully with the process according to the invention, describes the preparation of macromonomers of the general formula I

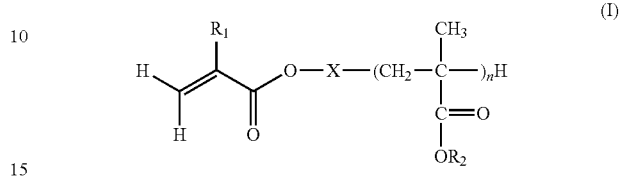

in which $R_1$ is hydrogen or methyl
X is a bivalent radical and
$R_2$ is an alkyl radical having from 1 to 40 carbon atoms, with the proviso that n is such that the molecular weight of the macromonomers 1 is in the range from 500 to 100 000 daltons,
by transesterifying monomeric esters of the formula II

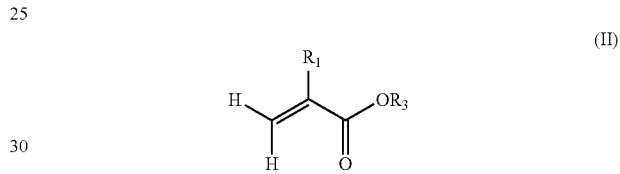

in which $R_1$ is as defined above and $R_3$ is an alkyl radical having from 1 to 8 carbon atoms with a hydroxyl-terminated polyalkyl methacrylate of the formula III

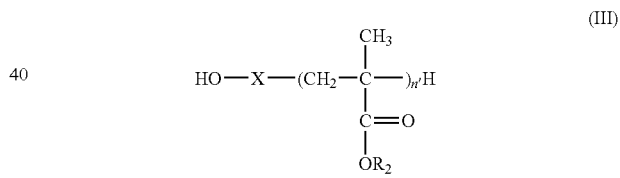

in which X and $R_2$ are each as defined above, with the proviso that n' corresponds to n with elimination of the alcohol $HOR_3$, to form the compound of the formula I.

The bivalent X radical is preferably a hydrocarbon chain which preferably has from 2 to 30 members, preferably with a —S— bridge directly adjoining the polymeric part of (I), where up to 9 carbon members may optionally be replaced by ether oxygen. In addition, in the X radical, the chain may also be interrupted by functional radicals of the formula:

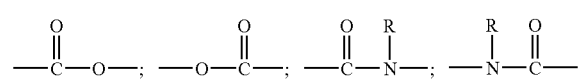

in which R is hydrogen or an alkyl radical having 1-8 carbon atoms, or a phenyl radical.

In addition, it is possible, through the process of the present invention, to obtain macromonomers which can be prepared by reacting functionalized polyolefins with carboxylic acids or carboxylic acid derivatives comprising carbon-carbon double bonds, for example (meth)acrylates or (meth)acrylic acid. Such monomers are described, for example, in EP-A-0 621 293 and EP-A-0 699 694. These monomers include at least one group which is derived from polyolefins. Polyolefins are known in the technical field, and can be obtained by polymerizing alkenes and/or alkadienes which consist of the elements hydrogen and carbon, for example ethylene, propylene, n-butene, isobutene, butadiene, isoprene. In this context, it is also possible to obtain, through suitable processes, polyolefins which have, for example, a hydroxyl or amino group which can be reacted with a carboxylic acid or a carboxylic acid derivative in accordance with the present process.

A further product class is that of compounds which can be used especially as plasticizers. These include esters of phthalic acid, isophthalic acid and terephthalic acid, which have at least one aliphatic alcohol radical, where the alcohol radical may have preferably from 1 to 40, and more preferably from 4 to 30 carbon atoms. These include especially di-2-ethylhexyl phthalate.

The inventive reaction takes place in the presence of at least one hydrolyzable catalyst. The expression "hydrolyzable" means that the catalyst reacts with water, preferably to form compounds which have poor solubility in the product ester. These catalysts are known per se and have been used for some time to prepare carboxylic esters and carboxamides.

These include especially catalysts which contain titanium, zirconium and hafnium, tin, aluminum and/or lead [cf. H. Rauch-Puntigam, Th. Völker, Acryl-und Methacrylverbindungen, p. 37-68, Springer-Verlag 1967, U.S. Pat. Nos. 2,138,763; 4,777,265; 5,210,177; EP-A 453 638; U.S. Pat. No. 4,745,213; EP-A 571 851; DE-A 43 01 673; U.S. Pat. Nos. 5,760,265; 4,505,091; DE-A 196 02 941; J. Org. Chem. 22 787-789 (1957)]. Preference is given here to using compounds which are soluble in the reaction medium.

Catalysts for use with preference include alkoxides, halides, nitrates, acetylacetonates and carboxylates of titanium, zirconium and hafnium, tin, aluminum and/or lead, preference being given especially to titanium, zirconium and hafnium.

Halides which can be used as catalysts include especially compounds of the titanium group, which include especially titanium, zirconium and hafnium. These include, for example, compounds of the formulae $MX_4$, $MX_3$, $MOX_2$, $RMX_3$ and $R_2MX_2$, in which M is Ti, Zr or Hf; X is a halogen atom and R is a hydrocarbon group, where the X and R radicals may be the same or different. R may be a linear or branched, saturated or unsaturated hydrocarbon group which may have a substituent, for example a halogen atom. R is preferably an aliphatic group, a cycloaliphatic group or an aromatic group, which has 1-40 carbon atoms, preferably 1-20 carbon atoms. The particularly preferred halide catalysts include $ZrCl_4$, $ZrCl_3$, $TiOCl_2$, $Ti(C_2H_5)_2 Cl_2$, $ZrOCl_2$, $Zr(C_2H_5)_2 Cl_2$ and $Zr(C_6H_5)_2 Cl_2$.

Examples of the nitrates include, for example, compounds of the titanium group, especially $MO(NO_3)_2$, $ROM(NO_3)_3$, $MR(NO_3)_3$ and $MR_2(NO_3)_2$, in which M is Ti, Zr or Hf and R is a hydrocarbon group. R is preferably an aliphatic group, a cycloaliphatic group or an aromatic group, which has 1-40 carbon atoms, preferably 1-20 carbon atoms.

The usable carboxylates include, for example, compounds of the titanium group, for example $M(R'COO)_4$, $O=M(R'COO)_2$, $R''O(R'COO)_3$, $(R''O)_2 M(R'COO)_2$, $R''M(R'COO)_3$ and $O=M(R'COCHCOO)$, in which M is Ti, Zr or Hf, R' and R'' are each hydrogen atoms or each independently hydrocarbon groups. R' and R'' may each independently be a linear or branched, saturated or unsaturated hydrocarbon group which may have a substituent, for example a halogen atom or a hydroxyl group. The carboxylate may be derived from a monobasic carboxylic acid, for example fumaric acid, malonic acid, tartaric acid, phthalic acid or trimellitic acid. Accordingly, the $(R''COO)_2$ group may be a radical bonded via a covalent bond. The R' and R'' radicals are preferably each aliphatic, cycloaliphatic or aromatic groups, which have 1-40 carbon atoms, preferably 1-20 carbon atoms.

Alkoxides which can be used as catalysts include, for example, compounds of the formulae $M(OR''')_4$ and $R'''O-[M(OR''')_2]_n-R'''$, in which M is Ti, Zr or Hf; n is an integer in the range from 1 to 20, preferably from 2 to 10 and most preferably from 4 to 8, and R''' is a hydrocarbon group, where the R''' radicals may be the same or different. R''' may be a linear or branched, saturated or unsaturated hydrocarbon group, which may have a substituent, for example a halogen atom. R''' is preferably an aliphatic group, a cycloaliphatic group or an aromatic group which has 1-40 carbon atoms, preferably 1-20 carbon atoms. The preferred catalysts include especially alkyl titanates, for example tetramethyl titanate $Ti(OMe)_4$, tetraisopropyl titanate $Ti(O-i-C_3H_7)_4$, tetrabutyl titanate $Ti(OC_4H_9)_4$, tetraoctyl titanate $Ti(OC_8H_{17})_4$, tetra-2-ethylhexyl titanate $Ti(O-i-C_8H_{17})_4$ or oligomeric alkyl titanates of the formula $C_4H_9O-[Ti(OC_4H_9)_4]_n-C_4H_9$, where n is selected such that the oligomeric alkyl titanate has a molar mass in the range from 1000 to 1500 g/mol. These catalysts are obtainable, for example, from DuPont™ under the trade name TYZOR® TPT, TYZOR® TnBT, TYZOR® BTP, TYZOR® TPT-20B (a mixture of 80% TYZOR® TPT and 20% TYZOR® TnBT), TYZOR® TOT and TYZOR® TIOT.

The preferred R, R', R'' and R''' radicals include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, isopropyl, tert-butyl, 2-methylpropyl, 2,2'-dimethylpropyl, 3-methylbutyl, 2-ethylhexyl, vinyl, allyl, 2-butenyl, 6-methyl-4-heptenyl, cyclopentyl, cyclohexyl, methylcyclohexyl, ethylcyclohexyl, cyclohexenyl, 1,3-cyclohexadienyl, phenyl, tolyl, benzyl, phenethyl and naphthyl.

The catalysts detailed above can be used individually or as a mixture. In addition, the compounds detailed above can first be reacted with the above-described reactants, especially the alcohols and/or amides, in order to obtain particularly preferred catalysts. After this reaction, by-products which are troublesome for further reactions can be removed before the use of the catalyst.

The reaction detailed above can take place under the known reaction conditions. Accordingly, the pressure or the temperature is not subject to any particular restriction. For instance, the reaction can be effected under elevated or reduced pressure, or else at standard pressure. Similarly, the reaction can be carried out at the customary temperatures, preference being given to temperatures in the range from 0 to 350° C., preferably from 50 to 250° C., according to the reactant.

During the reaction, the presence of water should be avoided as far as possible, in order to prevent premature hydrolysis of the catalyst. In general, however, small amounts of water can be tolerated. These should preferably not exceed 0.1% by weight, preferably 0.05% by weight and most preferably 0.03% by weight. The exact values depend especially on the hydrolysis sensitivity of the catalyst.

The specific reaction conditions are common knowledge, reference being made in this connection to the literature cited above. For instance, especially in the case of conversion of carboxylic acids or carboxylic acid derivatives which comprise polymerizable carbon-carbon double bonds, it is possible to add polymerization inhibitors which prevent undesired polymerization of the acids, esters or amides After the reaction, at least a portion of the catalyst used is hydrolyzed by the contacting with water. The higher the proportion of the hydrolyzed catalysts based on the total amount of catalyst, the better the removal of the catalyst from the reaction mixture subsequently succeeds. Accordingly, preferably at least 70%, more preferably at least 90% and most preferably at least 98% of the catalyst used is hydrolyzed.

The hydrolysis can be effected in the reaction mixture by adding water. In this case, the water can be effected before the addition of the superabsorbent, after addition of the superabsorbent or together with the superabsorbent. Preference is given to adding the water in the form of a moistened superabsorbent. The water can, for example, after the reaction of the carboxylic acid or of the carboxylic acid derivative with the alcohol or the amine has ended, be added to this reaction vessel.

In addition, the hydrolysis can also be effected in a separate reaction vessel, for example in a fixed bed reactor. In this case, the reaction mixture can be passed through a vessel, for example a column or a tube, which contains a moistened medium, preferably a water-comprising superabsorbent.

The amount of water which is used for the hydrolysis should be sufficient to enable very substantial hydrolysis. In one aspect of the present invention, it is possible, for example, to add at least 0.05% by weight, preferably at least 0.1% by weight, especially at least 0.2% by weight, preferably at least 0.5% by weight, more preferably at least 1% by weight and most preferably at least 2% by weight of water to the reaction mixture in order to hydrolyze the catalyst, the percentages being based on the weight of the reaction mixture. These amounts are based on the additionally added water, neglecting any water present in the reaction mixture. The exact water contents depend on the hydrolysis sensitivity of the catalyst, on the hydrolysis time and on the hydrolysis temperature. Small water contents may lead to a somewhat longer hydrolysis time. On the other hand, the amount of water added should be kept at a minimum in order not to exceed the water contents to be observed according to the specifications. In addition, excessively high water contents may lead to undesired side reactions. Surprisingly, the water contents can be kept particularly low by virtue of addition of a moistened superabsorbent.

The temperature at which the hydrolysis is performed is not subject to any general restriction. However, especially esters or amides which contain at least one double bond, for example the (meth)acrylates listed above, can polymerize. In order to minimize such polymerizations, the temperature can be selected at a low level. On the other hand, this can delay the hydrolysis. Accordingly, the hydrolysis temperature may preferably be within the range from 0 to 250° C., more preferably from 20 to 150° C. and most preferably from 40° C. to 100° C.

The duration of the hydrolysis may be within a wide range. The hydrolysis time is preferably at most 24 hours, preferentially at most 1 hour, and most preferably at most 30 minutes, without any intention that this should impose a restriction. In many cases, hydrolysis times of about 5, 10, 15 or 20 minutes are sufficient to achieve full hydrolysis. Particularly surprisingly, the hydrolysis time can be reduced if a water-containing superabsorbent is added to the reaction mixture.

The superabsorbents for use in accordance with the present invention are known in the technical field. The term "superabsorbent" is understood to mean especially a substance which can absorb a large amount of water without the substance being dissolved as a result. The term "absorbent" means that the superabsorbent can store the water, resulting in occurrence of a weight increase. The water is preferably retained by the superabsorbent even under a slight pressure of, for example, 80 g/cm² which is exerted on the moist superabsorbent.

Preferred superabsorbents are crosslinked polymers. These preferably include crosslinked polymers which comprise units of acrylic acid and/or methacrylic acid. These polymers comprise especially crosslinked polyacrylic acids or crosslinked starch-acrylic acid graft polymers, in which some of the carboxyl groups have been neutralized with sodium hydroxide solution or potassium hydroxide solution. Such polymers have been known for some time and are commercially available, for example, from Stockhausen GmbH & Co. KG. Particularly preferred superabsorbents are described, for example, in DE-A 199 09 838 and EP-A-0 574 260.

Preferred superabsorbents may comprise, for example, a) 55-99.9% by weight, preferably 70-90% by weight, of polymerized, ethylenically unsaturated, acid-containing monomers, which are neutralized to an extent of at least 25 mol %,
b) 0-40% by weight, preferably 0-20% by weight, of polymerized, ethylenically unsaturated monomers copolymerizable with a),
c) 0.1-5.0% by weight, preferably 0.1-3% by weight, of one or more polymerized crosslinking agents,
d) 0-30% by weight, preferably 0-5% by weight, of a water-soluble polymer, where the sum of the amounts by weight a) to d) is always 100% by weight.

The superabsorbents generally comprise at least one core crosslinker which prevents dissolution in water, but permits swelling. In addition, preferred superabsorbents are additionally surface crosslinked by a second crosslinking step. In this step, a second crosslinking agent is applied to the surface of superabsorbent polymer particles and crosslinked.

Preferred superabsorbents have, inter alia, a particle size in the range from 1 μm to 2000 μm, more preferably in the range from 40 μm to 900 μm. The superabsorbents may especially have a particle size in the range from 100 to 300 μm. The shape of the particles is unimportant, and the particles may be spherical or have an irregular shape. The particle size can be determined by screen analysis, at least 80% by weight of the particles having a size within the ranges of values specified.

In a particular aspect of the present invention, it is possible with preference to use superabsorbents with a block density in the range from 400 to 1000 g/l, more preferably from 500 to 750 g/l.

The absorption of preferred superabsorbents may be at least 10 g/g, more preferably at least 15 g/g, this value being determinable in accordance with EDANA 440.2-02 (ISO 17190-5:2001). This parameter depends on the salt content of the test solution. The values reported are based on an aqueous solution which contains 0.9% by weight of NaCl. The retention capacity of preferred superabsorbents may be at least 8 g/g, more preferably at least 15 g/g, this parameter being determinable at a pressure of 80 g/cm² with an aqueous solution which contains 0.9% by weight of NaCl. The retention capacity can be measured according to EDANA 441.2-02 (ISO 17190-6:2001) or EDANA 442.2-02 (ISO 17190-7: 2001).

Preferred superabsorbents have good swelling properties. After a swell time of 1 minute, the swell height may preferably be at least 3 mm, more preferably at least 4 mm. To measure the swell rate, demineralized water (DMW=<0.8 μs) can be used with preference. For example, for the determination, 0.2 g of superabsorbent can be distributed within a measuring cup. Subsequently, webs can be placed onto the polymer, such that a plunger is covered. Thereafter the superabsorbent can be moistened with demineralized water, such that the plunger is raised by the swelling of the superabsorbent. For the measurement, for example, 400 ml of water can be used, which serve to moisten the superabsorbent. The measurement can be carried out at 20° C. The rise of the plunger in mm is determined after 1 minute by means of a recorder.

A suitable superabsorbent can be obtained, for example, by polymerizing a) 55-99.9% by weight of a monounsaturated monomer having acid groups. Preference is given here to carboxyl-containing monomers, for example acrylic acid, methacrylic acid or 2-acrylamido-2-methylpropanesulfonic acid or mixtures of these monomers. It is preferred that at least 50% and more preferably at least 75% of the acid groups are carboxyl groups. The acid groups are generally neutralized to an extent of at least 25 mol %, i.e. are present in the form of sodium, potassium or ammonium salts. The degree of neutralization is preferably at least 50 mol %. Particular preference is given to a polymer which has been obtained by polymerizing acrylic acid or methacrylic acid, whose carboxyl groups have been neutralized to an extent of 50-80 mol % in the presence of crosslinkers.

The further monomers b) which may be used for the preparation of the absorbent polymers are 0-40% by weight of ethylenically unsaturated monomers copolymerizable with a), for example acrylamide, methacrylamide, hydroxyethyl acrylate, dimethylaminoalkyl (meth)acrylate, dimethyl aminopropylacrylamide or acrylamidopropyltrimethylammonium chloride. More than 40% by weight of these monomers can worsen the swellability of the polymers.

The crosslinker components c) used, which are present during the polymerization of a) and b), may be all compounds which bear at least two ethylenically unsaturated double bonds or one ethylenically unsaturated double bond and one functional group reactive toward acid groups of the monomers a) or several functional groups reactive toward acid groups. Examples include: aliphatic amides for example methylenebisacrylamide or -methacrylamide or ethylenebisacrylamide, and also aliphatic esters of polyols or alkoxylated polyols with ethylenically unsaturated acids, such as di(meth)acrylates or tri(meth)acrylates, butanediol or ethylene glycol, polyglycols, trimethylolpropane, di-and triacrylate esters of trimethylolpropane which has preferably been alkoxylated with from 1 to 30 mol of alkylene oxide, preferably ethoxylated, acrylate and methacrylate esters of glycerol and pentaerythritol, and of glycerol and pentaerythritol which have preferably been ethoxylated with from 1 to 30 mol of ethylene oxide, and also allyl compounds such as allyl (meth)acrylate, alkoxylated allyl (meth)acrylate reacted with preferably from 1 to 30 mol of ethylene oxide, triallyl cyanurate, diallyl maleate, polyallyl esters, tetraallyloxyethane, triallylamine, tetraallylethylenediamine, allyl esters of phosphoric acid or phosphorous acid, and also crosslinkable monomers, such as N-methylol compounds of unsaturated amides, such as of methacrylamide or acrylamide and the ethers derived therefrom. Mixtures of the crosslinkers mentioned can likewise be used. The proportion of the crosslinking comonomers is from 0.1 to 5% by weight, preferably from 0.01 to 3.0% by weight, based on the total amount of the monomers.

The water-soluble polymers d) which may be present, preferably in polymerized form, in the absorbent polymers are 0-30% by weight of water-soluble polymers, such as partly or fully hydrolyzed polyvinyl alcohol, polyvinylpyrrolidone, starch or starch derivatives, polyglycols or polyacrylic acids. The molecular weight of these polymers is uncritical provided that they are water-soluble. Preferred water-soluble polymers are starch and polyvinyl alcohol. The preferred content of such water-soluble polymers in the absorbent polymer is 0-30% by weight, preferably 0-5% by weight, based on the total amount of components a) to d). The water-soluble polymers, preferably synthetic polymers such as polyvinyl alcohol, may also serve as a graft base for the monomers to be polymerized.

To initiate the free-radical polymerization, the common initiators are used, for example azo or peroxo compounds, redox systems or UV initiators (sensitizers).

Superabsorbents for use with preference can be prepared, inter alia, by two methods:

In the first method the partly neutralized monomer a), preferably the acrylic acid, is converted, in aqueous solution, in the presence of crosslinkers and optionally further components, by free-radical polymerization to a gel, which is comminuted, dried, ground and screened off to the desired particle size. This solution polymerization can be carried out continuously or batchwise. The prior art features a broad spectrum of possible variations with regard to the concentration ratios, temperatures, type and amount of initiators. Typical processes are described in the following publications: U.S. Pat. No. 4,286,082, DE 27 06 135 and U.S. Pat. No. 4,076,663, whose disclosure on this subject is hereby introduced by reference.

Inverse suspension and emulsion polymerization can also be employed to prepare the inventive products. In these processes, an aqueous, partly neutralized solution of the monomers a), preferably acrylic acid, is dispersed with the aid of protective colloids and/or emulsifiers, in a hydrophobic organic solvent, and the polymerization is initiated by means of free-radical initiators. The crosslinkers are either dissolved in the monomer solution and metered in together with it, or else added separately and optionally during the polymerization. If appropriate, a water-soluble polymer d) is added as a graft base via the monomer solution or by direct incorporation into the oil phase initial charge. Subsequently, the water is removed azeotropically from the mixture and the polymer is filtered off and optionally dried. The crosslinking can be effected by copolymerizing a polyfunctional crosslinker dissolved in the monomer solution and/or by reacting suitable crosslinking agents with functional groups of the polymer during the polymerization steps. The processes are described, for example, in publications US 43 40 706, DE 37 13 601, DE 28 40 010 and WO 96/05234, whose disclosure on this subject is hereby introduced by reference.

The polymer gel is dried down to a water content of 0.5-25% by weight, preferably of from 1 to 10% by weight, more preferably from 1 to 8% by weight, at temperatures which are typically in the range of 100-200° C.

In a further step, the resulting polymers can be subjected to postcrosslinking.

The postcrosslinker components used may, for example, be polyols which react with the surface COOH groups of the polymer.

The polyols used may preferably be aliphatic polyhydroxyl compounds, such as $C_2$-$C_8$-alkylenediols, for example ethylene glycol, 1,3-propanediol, 1,4-butanediol, 1,5-pentanediol, 1,6-hexanediol, dianhydrosorbitol, $C_2$-$C_8$-alkylenetriols, for example glycerol, trimethylolpropane, higher-functional hydroxyl compounds, for example pentaerythritol and sugar alcohols, for example sorbitol, and also di-and polyalkylene glycols, for example diethylene glycol, dipropylene glycol, triethylene glycol, tetraethylene glycol, tetrapropylene glycol, polyethylene glycol, polypropylene glycol, polyglycols based on 2 or more different monomer units, for example a polyglycol composed of ethylene oxide and propylene oxide units.

In addition, it is possible to use polyepoxy compounds for surface crosslinking, for example ethylene glycol diglycidyl ether, diglyceryl diglycidyl ether, polyglyceryl polyglycidyl ether, propylene glycol diglycidyl ether and polypropylene glycol diglycidyl ether.

The postcrosslinker component or mixtures thereof are used in amounts of 0.01-5% by weight, preferably 0.1-2.5% by weight and more preferably from 0.5 to 1.5% by weight, based on the polymer to be crosslinked.

Postcrosslinker components can preferably be applied in the form of aqueous solutions. Suitable solvents are water and polar or nonpolar, water-miscible organic solvents, for example acetone, methanol, ethanol or 2-propanol, or mixtures thereof. The aqueous solution for preparing superabsorbents may, as well as water, also comprise organic solvents. The concentration of the particular postcrosslinker component in the aqueous solvent may vary within wide limits and is in the range from 1 to 80% by weight, preferably in the range from 5 to 65% by weight and most preferably within a range of from 10 to 40% by weight. The preferred solvent for the polyols as a postcrosslinking agent or the salt component is water, which is used in an amount of 0.5-10% by weight, preferably 0.75-5% by weight, and more preferably 1.0-4% by weight, based on the polymer.

The amount of superabsorbent which is used in accordance with the invention is not subject to any particular restriction. In general, it is possible, for example, to add at least 0.05% by weight, preferably at least 0.1% by weight, more preferably at least 1% by weight and most preferably at least 2% by weight, based on the total weight to the reaction mixture.

The superabsorbent can be added before, during or after the hydrolysis reaction. Preference is given to adding the superabsorbent to the reaction mixture together with the water in order to achieve rapid and reliable hydrolysis.

The weight ratio of superabsorbent to water is preferably in the range from 40:1 to 1:200, especially from 20:1 to 1:40, more preferably from 10:1 to 1:20 and most preferably in the range from 5:1 to 1:10.

After the hydrolysis, the superabsorbent can be removed from the reaction mixture by known processes, for example by filtration or decantation, especially by centrifugation, the hydrolyzed catalyst surprisingly being removed from the mixture together with the superabsorbent. Preferred parameters for the filtration or the centrifugation can be determined in a simple manner, simple routine experiments being sufficient. In comparison to the prior art, the pore size of the filter can be increased or the g number in the centrifugation can be reduced without this worsening the removal of the catalyst residues.

In the removal, it is possible to use customary filtration aids, for example silica gels or kieselguhr. In addition, it is surprisingly possible to increase the pH of the product slightly in a simple manner by adding basic substances to the filtration material or to the filtration aid in order to achieve the specifications of the product. Preference is given especially to basic substances which are insoluble in the product ester or the reaction mixture to be filtered. These include especially alkaline earth metal oxides, for example magnesium oxide MgO or calcium oxide CaO.

The metal of the catalyst can surprisingly be removed completely by the process according to the invention. There preferably remain in the product at most 50 ppm, more preferably at most 10 ppm and most preferably at most 5 ppm of metal in the product. This parameter can be determined in a known manner, for example via the color number, atomic emission spectroscopy, especially with inductively coupled plasma (ICP) or atomic absorption spectroscopy (AAS). The ICP method is described, for example, in detail in J. Nölte, "ICP-Emissionsspektroskopie für Praktiker" Wiley-VCH Verlag GmbH, Weinheim, 2002. An example of a particularly suitable spectrometer is an IRIS Intrepid II XDL ICP OES spectrometer from Thermo, for which instructions for procedure can be taken from the user's handbook "TEVA, Software zur ICP OES" from Thermo.

Overall, the present invention provides the use of superabsorbents for removing a metal-containing catalyst after a hydrolysis of the catalyst from a mixture. This novel and inventive use can be used especially to remove catalysts which comprise the metals listed above, especially titanium, zirconium, hafnium, tin or aluminum, in a simple and reliable manner from many reaction mixtures. The catalyst preferably precipitates out of the reaction mixture as a result of the hydrolysis and can therefore be removed together with the superabsorbent in a known manner, especially by filtration or centrifugation.

The present invention is illustrated in detail by examples hereinafter, without any intention that this should impose a restriction.

EXAMPLES 1 to 9 AND COMPARATIVE EXAMPLE 1

An ester prepared by means of tetraisopropyl titanate (TYZOR® TPT) is stirred with the moist superabsorbent in a closed 125 ml glass bottle for 30 minutes by means of a magnetic stirrer at 55° C., the amount of water and superabsorbent being shown in Table 1. The superabsorbents used are obtainable from Stockhausen GmbH & Co. KG. The solution is cooled without stirring in a water bath (approx. 20° C.) for 15 minutes and filtered twice through the same coarse 520A fluted filter (Schleicher & Schuell). The swollen superabsorbent beads remain in the filter, while the removal of the titanate is indicated by the disappearance of the color of the ester (orange). The amount of titanium was determined by means of ICP, the water content by means of Karl-Fischer titration. Table 1 which follows summarizes the results.

TABLE 1

| | Super-absorbent | Amount of super-absorbent [%[1]] | Amount of water [%[1]] | Content of Ti [ppm] | Water in the reaction mixture after the removal of the Ti [%] |
|---|---|---|---|---|---|
| Example 1 | Cabloc CTF ® | 0.1 | 0.1 | 4 | 0.07 |
| Comparative example 1 | — | — | — | 195 | 0.004 |
| Example 2 | Cabloc CTF ® | 1.0 | 1.0 | 1 | 0.1 |
| Example 3 | Cabloc CTF ® | 1.0 | 2.0 | 1 | 0.12 |
| Example 4 | Cabloc CTF ® | 0.5 | 1.0 | 1 | 0.12 |
| Example 5 | Cabloc CTF ® | 0.1 | 0.5 | 1 | 0.12 |
| Example 6 | Favor Pac 230 ® | 1.0 | 1.0 | 1 | 0.1 |
| Example 7 | Favor Pac 230 ® | 1.0 | 2.0 | 1 | 0.11 |
| Example 8 | Favor Pac 230 ® | 0.5 | 1.0 | 1 | 0.12 |
| Example 9 | Favor Pac 230 ® | 0.1 | 0.5 | 1 | 0.12 |

[1]The percentage is based on the weight of the reaction mixture

EXAMPLES 10 to 15

In a further test series, the catalyst was removed by a pressure filtration. In this series, the crude ester admixed with moist superabsorbent was forced by means of compressed air of not more than 2 bar through filters of different pore size. A Seitz EF 14/2 pressure filter apparatus (volume 2.2 l; heatable) was used.

To this end, 500 g of crude ester and the amount of superabsorbent shown in Table 2 were initially charged in a 2 l flask. The superabsorbents used are obtainable from Stockhausen GmbH & Co. KG. Subsequently, the amount of water stated in Table 2 was added with stirring. Subsequently, the catalyst was hydrolyzed at 90° C. for 30 minutes. The reaction mixture was then cooled within 15 minutes to a temperature of less than 30° C. with a water bath (20° C.) and filtered under pressure. The maximum pressure in the filtration was 2 bar, and the mixture was filtered twice through the same filter.

The swollen superabsorbent beads remain in the filter, while the removal of the titanate is indicated by the disappearance of the color of the ester (orange). The amount of titanium was determined by means of ICP, the water content by means of Karl-Fischer titration and the acid number by means of a KOH titration to DIN 53402. Table 2 which follows summarizes the results.

TABLE 2

| | Superabsorbent used | Amount of superabsorbent [%[1]] | Amount of water [%[1]] | Filter material |
|---|---|---|---|---|
| Example 10 | Cabloc CTF ® | 5 | 10 | Seitz T500 (pore size 3-8 µm) |
| Example 11 | Cabloc CTF ® | 5 | 10 | Seitz T750 (pore size 5-10 µm) |
| Example 12 | Cabloc CTF ® | 5 | 10 | Seitz T1000 (pore size 9-25 µm) |
| Example 13 | Favor Pac 230 ® | 5 | 10 | Seitz T500 |
| Example 14 | Favor Pac 300 ® | 5 | 10 | Seitz T500 |
| Example 15 | Cabloc CT ® | 1 | 2 | Seitz T500 |

| | Acid number [mg KOH/g] | Content of Ti [ppm] | Water in the reaction mixture after the removal of the Ti [%] |
|---|---|---|---|
| Example 10 | 0.12 | <1 | 0.12 |
| Example 11 | 0.14 | <1 | 0.12 |
| Example 12 | 0.11 | 2 | 0.12 |
| Example 13 | 0.08 | <1 | 0.11 |
| Example 14 | 0.13 | <1 | 0.12 |
| Example 15 | 0.08 | <1 | 0.1 |

[1]The percentage is based on the weight of the reaction mixture

EXAMPLES 16 to 26 And COMPARATIVE EXAMPLE 2

An ester prepared by means of tetraisopropyl titanate (TYZOR® TPT) is stirred with the moist superabsorbent by means of a magnetic stirrer in a closed 125 ml glass bottle, the amount of water and superabsorbent added and the hydrolysis time and hydrolysis temperature being shown in Table 3. The superabsorbent used was Cabloc CTF®, which has a particle size in the range from 50 to 200 µm and is obtainable from Stockhausen GmbH & Co. KG. The solution is cooled without stirring in a water bath (approx. 20° C.) for 15 minutes and filtered twice through the same coarse 520A fluted filter (Schleicher & Schuell). The swollen superabsorbent beads remain in the filter, while the removal of the titanate is indicated by the disappearance of the color of the ester (orange). The amount of titanium was determined by means of ICP, the water content by means of Karl-Fischer titration and the acid number by means of a KOH titration to DIN 53402. Table 3 which follows summarizes the results.

TABLE 3

| | Amount of superabsorbent [%[1]] | Amount of water [%[1]] | Hydrolysis time [min] | Hydrolysis temperature [° C.] |
|---|---|---|---|---|
| Example 16 | 0.1 | 0.2 | 60 | 55 |
| Comparative example 2 | — | — | — | — |
| Example 17 | 0.15 | 0.75 | 30 | 55 |
| Example 18 | 0.1 | 0.5 | 30 | 55 |
| Example 19 | 0.2 | 0.4 | 30 | 55 |
| Example 20 | 0.2 | 0.4 | 60 | 55 |
| Example 21 | 0.1 | 0.2 | 60+ | RT[2] |
| Example 22 | 0.05 | 0.25 | 60+ | RT[2] |
| Example 23 | 0.15 | 0.3 | 30 | 55 |
| Example 24 | 0.15 | 0.3 | 60 | 55 |
| Example 25 | 0.1 | 0.3 | 30 | 55 |
| Example 26 | 0.1 | 0.4 | 30 | 55 |

| | Acid number [mg KOH/g] | Content of Ti [ppm] | Water in the reaction mixture after removal of the Ti [%] |
|---|---|---|---|
| Example 16 | 0.07 | 2 | 0.09 |
| Comparative example 2 | 0.12 | 200 | 0.004 |
| Example 17 | 0.06 | 1 | 0.11 |
| Example 18 | 0.07 | 3 | 0.11 |
| Example 19 | 0.06 | 4 | 0.11 |
| Example 20 | 0.06 | 1 | 0.09 |
| Example 21 | 0.04 | 1 | 0.06 |
| Example 22 | 0.06 | 1 | 0.09 |
| Example 23 | 0.06 | 3 | 0.11 |
| Example 24 | 0.05 | 1 | 0.08 |
| Example 25 | 0.06 | 3 | 0.08 |
| Example 26 | 0.01 | 2 | 0.11 |

[1]The percentage is based on the weight of the reaction mixture
[2]RT = room temperature, approx. 20° C.

EXAMPLES 27 to 33

In a further test series, the catalyst was removed by a pressure filtration. In this series, the hydrolyzed, superabsorbent-containing crude ester was forced through a Seitz T500 filter (pore size 3-8 µm) by means of compressed air of not more than 2 bar. A Seitz EF 14/2 pressure filter apparatus (volume 2.2 l; heatable) was used.

In Examples 27, 29 to 32 the superabsorbent used was Cabloc CTF®, which has a particle size in the range from 50 to 200 µm and is obtainable from Stockhausen GmbH & Co. KG. In Examples 28 and 33, the superabsorbent used was Favor Pac 300®, which has a particle size in the range from 150 to 860 µm and is obtainable from Stockhausen GmbH & Co. KG. In Examples 27, 29 to 33 a superabsorbent moistened with an amount of water specified in Table 4 was added to the reaction mixture, similarly to the examples described above. In Example 28, first the superabsorbent and then the water were stirred into the reaction mixture. The particular amounts of superabsorbent and water, and the hydrolysis time and hydrolysis temperature are specified in Table 4, 500 g of crude ester having been initially charged in a 1 l flask in Examples 27 to 30, whereas 1000 g of crude ester in a 4 l flask were used in Examples 31 to 33.

The solution is cooled to a temperature of less than 30° C. without stirring in a water bath (approx. 20° C.) for 15 minutes and filtered under pressure. The maximum pressure in the filtration was 2 bar, and the mixture was filtered twice through the same filter. The swollen superabsorbent beads remain in the filter, while the removal of the titanate is indicated by the disappearance of the color of the ester (orange). The amount of titanium was determined by means of ICP, the water content by means of Karl-Fischer titration and the acid number by means of a KOH titration to DIN 53402. Table 4 which follows summarizes the results.

TABLE 4

| | Amount of super-absorbent [%[1]] | Amount of water [%[1]] | Hydrolysis time [min] | Hydrolysis temperature [° C.] |
|---|---|---|---|---|
| Example 27 | 1 | 2 | 30 | 55 |
| Example 28 | 5 | 10 | 30 | 55 |
| Example 29 | 0.5 | 1 | 30 | 90 |
| Example 30 | 0.12 | 0.48 | 30 | 90 |
| Example 31 | 0.5 | 1 | 30 | 90 |
| Example 32 | 0.1 | 0.5 | 30 | 90 |
| Example 33 | 0.1 | 0.5 | 30 | 55 |

| | Content of Ti [ppm] | Water in the reaction mixture after removal of the Ti [%] |
|---|---|---|
| Example 27 | <1 | 0.13 |
| Example 28 | <1 | 0.12 |
| Example 29 | <1 | 0.13 |
| Example 30 | <1 | 0.08 |
| Example 31 | <1 | 0.16 |
| Example 32 | <1 | 0.08 |
| Example 33 | <1 | 0.14 |

[1]The percentage is based on the weight of the reaction mixture

EXAMPLES 34 to 38

In addition, different esters were prepared by transesterifying methyl methacrylate with alcohol mixtures, catalyzed by tetraisopropyl titanate (TYZOR® TPT). After the transesterification, the catalyst was removed by a pressure filtration. In this filtration, the crude ester admixed with moist superabsorbent was forced by means of compressed air of not more than 2 bar through filters of different pore size. A Seitz EF 14/2 pressure filter apparatus (capacity 2.2 l; heatable) with a filter material comprising Seitz T500/Seitz KS80/0.1% by weight of Decalite was used. In Example 37, 0.01% by weight of CaO was additionally added to the filter material.

In this case, 500 g of crude ester were admixed with the amounts of water-containing superabsorbent specified in Table 5, and stirred at 90° C. for 90 minutes. Subsequently, the solution was cooled to a temperature of less than 30° C. without stirring in a water bath (approx. 20° C.) for 15 minutes and filtered under pressure. The maximum pressure in the filtration was 2 bar, and the mixture was filtered twice through the same filter. The swollen superabsorbent beads remain in the filter, while the removal of the titanate is indicated by the disappearance of the color of the ester (orange). The amount of titanium was determined by means of ICP with an IRIS Intrepid II XDL ICP OES spectrometer from Thermo, the water content by means of Karl-Fischer titration, the color number to ASTM D1500 and the acid number by means of a KOH titration to DIN 53402. Table 5 which follows summarizes the results.

TABLE 5

| | Ester prepared | Superabsorbent used | Amount of superabsorbent [%[1]] | Amount of water [%[1]] |
|---|---|---|---|---|
| Example 34 | i-C10-methacrylate | Cabloc CTF ® | 0.05 | 0.1 |
| Example 35 | C10-C16-methacrylate | Favor Pac 300 ® | 0.1 | 0.2 |
| Example 36 | C12-C20-methacrylate | Cabloc CTF ® | 0.15 | 0.3 |
| Example 37 | C12-C20-methacrylate | Cabloc CTF ® | 0.1 | 0.2 |
| Example 38 | C12-C14-methacrylate | Favor Pac 300 ® | 0.1 | 0.2 |

| | Acid number [mg KOH/g] | Content of Ti [ppm] | Water in the reaction mixture after the removal of the Ti [%] | Color number |
|---|---|---|---|---|
| Example 34 | 0.10 | <1 | 0.05 | 0 |
| Example 35 | 0.13 | <1 | 0.05 | 0 |
| Example 36 | 0.08 | <1 | 0.02 | 0 |
| Example 37 | 0.14 | <1 | 0.02 | 0 |
| Example 38 | 0.12 | <1 | 0.06 | 0 |

[1]The percentage is based on the weight of the reaction mixture

Surprisingly, especially the comparison of Example 36 with Examples 35 and 37 shows that addition of CaO in the filter material allows the acid number to be reduced.

The invention claimed is:

1. A process for preparing carboxylic acid derivatives, comprising the reaction of at least one carboxylic acid, a carboxylic acid ester, a carboxamide and a carboxylic acid anhydride with at least one alcohol and/or an amine in the presence of a metal-containing catalyst, wherein after the reaction has ended, the metal-containing catalyst is contacted with water in the presence of a crosslinked polymer superabsorbent, said contacting of the catalyst with the water leading to hydrolysis of the catalyst.

2. The process as claimed in claim 1, wherein said crosslinked polymer comprises units derived from acrylic acid and/or methacrylic acid.

3. The process as claimed in claim 1, wherein said superabsorbent has a particle size in the range from 40 to 900 μm.

4. The process as claimed in claim 1, wherein hydrolysis of the catalyst takes place by addition of water to the reaction mixture.

5. The process as claimed in claim 1, wherein for the hydrolysis, an amount of water of at least 0.05% by weight based on the total weight of the reaction mixture is added.

6. A process for preparing carboxylic acid derivatives, comprising the reaction of at least one of a carboxylic acid, a carboxylic acid ester, a carboxamide and a carboxylic acid anhydride with at least one alcohol and/or an amine in the presence of a metal-containing catalyst, wherein after the reaction has ended, the metal-containing catalyst is contacted with water and a crosslinked polymer superabsorbent, said contacting of the catalyst with the water leading to hydrolysis of the catalyst, wherein for the hydrolysis, a water-containing superabsorbent is used.

7. The process as claimed in claim 1, wherein a weight ratio of superabsorbent to water is in the range from 10:1 to 1:20.

8. The process as claimed in claim 1, wherein for the hydrolysis, a column filled with water-containing superabsorbent is used.

9. The process as claimed in claim 1, wherein hydrolysis is effected at a temperature in the range from 40° C. to 90° C.

10. The process as claimed in claim 1, wherein hydrolysis lasts for at most 1 hour.

11. The process as claimed in claim 1, wherein the product of the reaction comprises a polymerizable double bond.

12. The process as claimed in claim 11, wherein the reaction is performed in the presence of a polymerization inhibitor.

13. The process as claimed in claim 11, wherein (meth) acrylic acid, maleic acid and/or fumaric acid or an ester of these carboxylic acids is used as the reactant.

14. The process as claimed in claim 13, wherein an ester of (meth)acrylic acid whose alcohol radical has from 1 to 6 carbon atoms is used.

15. The process as claimed in claim 13, wherein a methyl ester, ethyl ester, propyl ester and/or butyl ester of (meth) acrylic acid is used.

16. The process as claimed in claim 1, wherein the reactant used is an alcohol and/or an amine having from 1 to 40 carbon atoms.

17. The process as claimed in claim 1, wherein the reactant used is a polymeric compound having a weight-average molecular weight $M_w$ in the range from 500 to 100 000 g/mol, said compound having at least one hydroxyl and/or amine functionality.

18. The process as claimed in claim 1, wherein the metal-containing catalyst comprises titanium or zirconium.

19. The process as claimed in claim 18, wherein the catalyst used is a titanium alkoxide.

* * * * *